(12) United States Patent
Capel et al.

(10) Patent No.: US 11,523,995 B2
(45) Date of Patent: Dec. 13, 2022

(54) COMPOSITIONS AND METHODS FOR ABLATING NICHE CELLS IN TESTIS AND OTHER EPITHELIAL CELLS AND METHODS RELATING THERETO

(71) Applicant: Duke University, Durham, NC (US)

(72) Inventors: Blanche Capel, Chapel Hill, NC (US); Jennifer McKey, Chapel Hill, NC (US); Tetsuhiro Yokonishi, Durham, NC (US)

(73) Assignee: Duke University, Durham, NC (US)

( * ) Notice: Subject to any disclaimer, the term of this patent is extended or adjusted under 35 U.S.C. 154(b) by 114 days.

(21) Appl. No.: 16/767,491

(22) PCT Filed: Nov. 30, 2018

(86) PCT No.: PCT/US2018/063374
§ 371 (c)(1),
(2) Date: May 27, 2020

(87) PCT Pub. No.: WO2019/108973
PCT Pub. Date: Jun. 6, 2019

(65) Prior Publication Data
US 2020/0345667 A1    Nov. 5, 2020

Related U.S. Application Data (60) Provisional application No. 62/672,341, filed on May 16, 2018, provisional application No. 62/670,130, filed on May 11, 2018, provisional application No. 62/592,469, filed on Nov. 30, 2017.

(51) Int. Cl.
| | | |
|---|---|---|
| *A61K 31/14* | (2006.01) | |
| *A61P 15/08* | (2006.01) | |
| *A61K 35/52* | (2015.01) | |

(52) U.S. Cl.
CPC .............. *A61K 31/14* (2013.01); *A61K 35/52* (2013.01); *A61P 15/08* (2018.01)

(58) Field of Classification Search
CPC .......... A61K 31/14; A61K 35/52; A61K 9/08; A61P 15/08; A61P 35/00
See application file for complete search history.

(56) References Cited

U.S. PATENT DOCUMENTS

2003/0099726 A1*  5/2003  Squires ................. A61K 36/28
                                                              424/754
2016/0151541 A1   6/2016  Hasilo et al.

OTHER PUBLICATIONS

Maymon et al., "Sertoli cell inactivation by cytotoxic damage to the human testis after cancer chemotherapy," Fertil. Steril. May 2004;81(5):1391-94. PMID: 15136109. (Year: 2004).*
Shinohara et al., "Restoration of Spermatogenesis in Infertile Mice by Sertoli Cell Transplantation", Biology of Reproduction, 2003, 68(3), 1064-1071.
Shinohara et al., "Rats produced by interspecies spermatogonial transplantation in mice and in vitro microinsemination", PNAS, 2006, 103(37), 13624-13628.
Zucoloto et al., "Effect of chemical ablation of myenteric neurones on intestinal cell proliferation", Cell Tissue Kinet., 1988, vol. 21, 213-219.
Kawa et al., "Restoration of spermatogenesis by lentiviral gene transfer: Offspring from infertile mice", PNAS, 2002, 99(11), 7524-7529.
Ogawa et al., "Transplantation of male germ line stem cells restores fertility in infertile mice", Nat. Med., 2000, 6(1), 29-34.
Avarbock M.R., et al., "Reconstitution of Spermatogenesis From Frozen Spermatogonial Stem Cells," National Library of Medicine, Jun. 1996, vol. 2, No. 6, pp. 693-696.
Brinster R.L., et al., "Spermatogenesis following Male Germ-Cell Transplantation," Proceedings of the National Academy of Sciences, USA, 1994, vol. 91, No. 24, pp. 11298-11302.
Brook P.F., et al., "Isolation of Germ Cells From Human Testicular Tissue for Low Temperature Storage and Autotransplantation," Fertility and sterility, Feb. 2001, vol. 75, No. 2, pp. 269-274.
Buganim Y., et al., "Direct Reprogramming of Fibroblasts into Embryonic Sertoli-like Cells by Defined Factors," Cell Stem Cell, Sep. 2012, vol. 11, No. 3, pp. 373-386.
Dobrinski I., et al., "Germ Cell Transplantation from Large Domestic Animals into Mouse Testes," Molecular Reproduction and Development, 2000, vol. 57, No. 3, pp. 270-279.
Dobrinski I., et al., "Transplantation of Germ Cells from Rabbits and Dogs into Mouse Testes," Biology of Reproduction, 1999, vol. 61, No. 5, pp. 1331-1339.
Fox D.A., et al., "Selective Myenteric Neuronal Denervation of the Rat Jejunum. Differential Control of the Propagation of Migrating Myoelectric Complex and Basic Electric Rhythm," Gastroenterology, 1984, vol. 87, No. 3, pp. 572-577.
International Preliminary Report on Patentability for International Application No. PCT/US2018/063374, dated Jun. 11, 2020, 10 pages.
International Search Report and Written Opinion for International Application No. PCT/US2018/063374, dated Apr. 22, 2019, 12 pages.
Jungwirth A., et al., "European Association of Urology Guidelines on Male Infertility: The 2012 update," European Urology, Aug. 2012, vol. 62, No. 2, pp. 324-332.

(Continued)

*Primary Examiner* — Theodore R. Howell
(74) *Attorney, Agent, or Firm* — Polsinelli PC (57) ABSTRACT

The present disclosure relates to compositions and methods for ablating epithelial cells, in particular to methods for ablating Sertoli cells in testis, and methods related thereto. In particular, the present disclosure relates to methods for ablating Sertoli and other cells in the testis using benzalkonium chloride, to methods for rescuing endogenous spermatogenesis in a subject suffering from Sertoli cell dysfunction, to methods of reconstructing spermatogenesis, to methods of treating infertility, and to methods for the selective depletion of epithelial cells in a tissue and for the treatment of diseases or disorders associated with damaged epithelial cells.

12 Claims, 5 Drawing Sheets

(56) References Cited

OTHER PUBLICATIONS

Kanatsu-Shinohara M., et al., "Adenovirus-Mediated Gene Delivery and in Vitro Microinsemination Produce Offspring from Infertile Male Mice," Proceedings of the National Academy of Sciences, USA, 2002, vol. 99, No. 3, pp. 1383-1388.
Kanatsu-Shinohara M., et al., "Germline Niche Transplantation Restores Fertility in Infertile Mice," Human Reproduction, 2005, vol. 20, No. 9, pp. 2376-2382.
Kumar R., et al., "Drug Therapy for Idiopathic Male Infertility: Rationale Versus Evidence," Journal of Urology, Oct. 2006, vol. 176(4 Pt 1), pp. 1307-1312.
Marettová E., et al., "Toxic Effects of Cadmium on Testis of Birds and Mammals: A Review," Animal Reproduction Science, Apr. 2015, vol. 155, pp. 1-10.
Marple B., et al., "Safety Review of Benzalkonium Chloride Used as a Preservative in Intranasal Solutions: an Overview of Conflicting Data and Opinions," Otolaryngology—Head and Neck Surgery, Jan. 2004, vol. 130, No. 1, pp. 131-141.
Nagano M., et al., "Long-Term Survival of Human Spermatogonial Stem Cells in Mouse Testes," Fertility and Sterility, Dec. 2002, vol. 78, No. 6, pp. 1225-1233.
Pan W.K., et al., "Transplantation of Neonatal Gut Neural Crest Progenitors Reconstructs Ganglionic Function in Benzalkonium Chloride-treated Homogenic Rat Colon,"Journal of Surgical Research, May 15, 2011, vol. 167, No. 2, pp. e221-e230.
Rebourcet D., et al., "Sertoli Cells Control Peritubular Myoid Cell Fate and Support Adult Leydig Cell Development in the Prepubertal Testis," Development, May 2014, vol. 141, No. 10, pp. 2139-2149.
Rebourcet D., et al., "Sertoli Cells Maintain Leydig Cell Number and Peritubular Myoid Cell Activity in the Adult Mouse Testis," PLoS One, Aug. 2014, vol. 9, No. 8, e105687, pp. 1-13.
Sakata K., et al., "Selective Destruction of Intestinal Nervous Elements by Local Application of Benzalkonium Solution in the Rat," Experientia, Dec. 1979, vol. 35, No. 12, pp. 1611-1613.
Sasaki K., et al., "Robust in Vitro Induction of Human Germ Cell Fate From Pluripotent Stem Cells," Cell Stem Cell, Aug. 2015, vol. 17, No. 2, pp. 178-194.
Sato A., et al., "Pathophysiology of Aganglionic Colon and Anorectum: An Experimental Study on Aganglionosis Produced by a New Method in the Rat," Journal of Pediatric Surgery, Aug. 1978, vol. 13, No. 4, pp. 399-435.
Sato T., et al., "Testis Tissue Explantation Cures Spermatogenic Failure in C-kit Ligand Mutant Mice," PNAS, USA, Oct. 16, 2012, vol. 109, No. 42, pp. 16934-16938.
Schwartz L.A., et al., "Self-reported Health Problems of Young Adults in Clinical Settings: Survivors of Childhood Cancer and Healthy Controls," Journal of the American Board of Family Medicine, May-Jun. 2010, vol. 23, No. 3, pp. 306-314.
Shinomura M., et al., "A Novel Amh-treck Transgenic Mouse Line Allows Toxin-dependent Loss of Supporting Cells in Gonads," Reproduction, Dec. 2014, vol. 148, No. 6, pp. H1-H9.
Shu X., et al., "Treatment of Aganglionic Megacolon Mice via Neural Stem Cell Transplantation," Molecular Neurobiology, Dec. 2013, vol. 48, No. 3, pp. 429-437, DOI: 10.1007/s12035-013-8430-x.
Watanabe S., et al., "Adeno-Associated Virus-mediated Delivery of Genes to Mouse Spermatogonial Stem Cells," Biology of Reproduction, Jan. 2017, vol. 96, No. 1, pp. 221-231.
Watanabe S., et al., "In Vivo Genetic Manipulation of Spermatogonial Stem Cells and Their Microenvironment by Adeno-associated Viruses," Stem Cell Reports, May 8, 2018, vol. 10, No. 5, pp. 1551-1564.
Wyns C., et al., "Long-term Spermatogonial Survival in Cryopreserved and Xenografted Immature Human Testicular Tissue," Human Reproduction, Nov. 1, 2008, vol. 23, No. 11, pp. 2402-2414.
Yokonishi T., et al., "In Vitro Spermatogenesis Using an Organ Culture Technique," Methods in Molecular Biology, 2013, vol. 927, pp. 479-488.
Yokonishi T., et al., "Offspring Production With Sperm Grown in Vitro From Cryopreserved Testis Tissues," Nature Communications, Jul. 2014, vol. 5, No. 4320, 6 pages.
Yoneda A., et al., "Selective Chemical Ablation of the Enteric Plexus in Mice," Pediatric Surgery International, May 2002, vol. 18, No. 4, pp. 234-237.
Yumura Y., et al., "Nationwide Survey of Urological Specialists Regarding Male Infertility: Results from a 2015 Questionnaire in Japan," Reproductive Medicine and Biology, Oct. 2017, vol. 17, No. 1, pp. 44-51.

* cited by examiner

COMPOSITIONS AND METHODS FOR ABLATING NICHE CELLS IN TESTIS AND OTHER EPITHELIAL CELLS AND METHODS RELATING THERETO

CROSS REFERENCE TO RELATED APPLICATIONS

This application is the US national phase under 35 U.S.C. § 371 of International Application No. PCT/US2018/063374, filed Nov. 30, 2018, which claims priority to U.S. Provisional Patent Application Ser. Nos. 62/592,469, filed Nov. 30, 2017, 62/670,130, filed May 11, 2018, and 62/672,341, filed May 16, 2018, the contents of each of which are hereby incorporated by reference in their entirety.

BACKGROUND OF THE INVENTION

Field of the Invention

The present disclosure relates to compositions and methods of ablating epithelial cells, in particular to methods of ablating Sertoli cells in testis. The present disclosure also relates to methods of treating male infertility.

Description of the Related Art

Infertility affects an estimated 10-15% of couples and in 45-50% of these cases, the defect lies with the male partner (Jungwirth, A., et al. *Eur Urol* 62: 324-332 (2012)). Approximately 1:100 adult males is clinically infertile, and approximately 40% (the largest proportion) of cases are idiopathic. Current drug therapies for idiopathic patients have limited effectiveness and are controversial (Kumar, R., et al. *J Urol* 176: 1307-1312 (2006); Yumura, Y., et al. *Reproductive Medicine and Biology* 17: 44-51 (2018)).

Spermatogenesis requires the orchestrated support from the surrounding somatic cells in the testis. Spermatogonial stem cells (SSCs) proliferate, differentiate, and produce sperm throughout the male lifetime. SSCs are tightly controlled inside a germ cell niche composed of Sertoli cells, Leydig cells, peritubular myoid cells (PMCs), macrophages and vasculature. Although the testis contains various somatic cells outside the seminiferous cords, including Leydig cells, PMCs and macrophages, the inner tubules of the mammalian testis contain only two populations of cells: SSCs and their descendent developing sperm, and Sertoli cells that are essential to protect and support the SSCs. Sertoli cells interact directly with germ cells and are vital to provide morphological and nutritional support for spermatogenesis. For this reason, their dysfunction is often the cause of spermatogenic failure (Kanatsu-Shinohara, M., et al. *Hum Reprod* 20: 2376-2382 (2005)). And while defects in Sertoli cells and other somatic cell types that form the SSC niche in the testis are responsible for many cases of infertility, it has been difficult to repair or replace these cells.

To compensate for Sertoli cell dysfunction, several therapeutic experiments have been reported such as transplantation of healthy Sertoli cells (Id.), addition of missing growth factors by viral transduction (Ikawa, M., et al. *Proc Natl Acad Sci USA* 99: 7524-7529 (2002); Kanatsu-Shinohara, M., et al. *Proc Natl Acad Sci USA* 99: 1383-1388 (2002); Watanabe, S., et al. *Stem cell reports* 10: 1551-1564 (2018)), or explant and culture of testis tissue in vitro (Sato, T., et al. *Proc Natl Acad Sci USA* 109: 16934-16938 (2012)). Because introduction of viruses can be dangerous, and a human testis culture system has not been established, Sertoli cell transplantation is currently the most realistic approach for the clinic.

Very recently Shinohara and his colleague reported using an adeno-associated-virus (AAV) system to overcome the inflammation problems associated with adenovirus (Watanabe, S., et al. *Biol Reprod* 96: 221-231 (2017)). Although they showed offspring did not carry the AAV genome by southern blotting and PCR, AAV transmission to the next generation remains a danger.

Efforts to replace defective Sertoli cells have been hampered by the inability to achieve engraftment in competition with resident cells. Ablation of Sertoli cells was previously reported using diphtheria toxin receptor-mediated conditional and targeted cell ablation gene editing systems (Shinomura, M., et al. *Reproduction* 148: H1-9 (2014); Rebourcet, D., et al. *PLoS One* 9: e105687 (2014); Rebourcet, D., et al. *Development (Cambridge, England)* 141: 2139-2149 (2014)). These methods have significantly advanced knowledge of testis biology but are not feasible for the clinic.

The $Kitl^{Sl/Sld}$ mutant mouse, which is a model of infertility due to Sertoli cell dysfunction, was used previously to test the idea that Sertoli cell transplantation could rescue spermatogenesis (Kanatsu-Shinohara, M., et al. *Hum Reprod* 20: 2376-2382 (2005)). However, the efficiency of donor Sertoli cell engraftment was not high. To increase transplantation efficiency, one study used cadmium to ablate Sertoli cells (Shinohara, T., et al. *Biol Reprod* 68: 1064-1071 (2003)), but the effect of cadmium was not limited to Sertoli cells (Marettova, E., et al. *Animal Reproduction Science* 155: 1-10 (2015)) and injecting cadmium in a clinical situation is not a feasible approach. Other groups used new transgenic mouse models expressing cytotoxic genes or specific toxin receptors to eliminate Sertoli cells (Shinomura, M., et al. *Reproduction* 148: H1-9 (2014)). Because this technique is based on transgenic technology or genome editing, this is also not realistic for clinical application.

Pediatric cancer survivors represent a second major source of male infertility. Because of significant advances in cancer treatment, one out of every 640 young adults is a pediatric cancer survivor (Schwartz, L. A., et al. *J Am Board Fam Med* 23: 306-314 (2010)), and 30% of these suffer from infertility as adults. Cryopreservation of immature testis tissue or SSCs in advance of cancer therapy might benefit these patients, but there is a significant risk of cancer recurrence due to contamination when cryopreserved tissue fragments are transplanted back into the patient. Despite this risk, several groups have experimented with testicular grafting of a small piece of immature testis tissue. Wyns et al. reported that cryopreserved tissues from pre-pubertal cancer patients were later thawed and xeno-transplanted into the scrotum of nude mice (Wyns, C., et al. *Hum Reprod* 23: 2402-2414 (2008)). These xenografts survived more than 6 months, but did not achieve complete sperm maturation. Healthy sperm was previously obtained from in vitro cultured neonatal mouse testis tissues after cryopreservation (Yokonishi, T., et al. *Nat Commun* 5: 4320 (2014)), however a human culture system has not been established.

SUMMARY OF THE INVENTION

In one aspect, the present invention provides a method for ablating Sertoli cells in a subject comprising administering to the subject an effective amount of benzalkonium chloride (BC). In certain embodiments, selective Sertoli cell ablation is achieved at Day 4 following administration of the BC.

In a second aspect, the present invention provides a method for rescuing endogenous spermatogenesis in a subject suffering from Sertoli cell dysfunction comprising ablating the endogenous Sertoli cells of the subject and subsequently transplanting donor Sertoli cells into the testis of the subject.

In a third aspect, the present invention provides a method for treating infertility in a subject comprising ablating the endogenous Sertoli cells of the subject and subsequently transplanting donor Sertoli cells into the testis of the subject, wherein endogenous spermatogenesis is induced in the subject.

In a fourth aspect, the present invention provides a method of reconstructing spermatogenesis of a subject comprising ablating the endogenous Sertoli and germ cells of the subject and subsequently transplanting previously collected testicular cells of the subject into the testis of the subject. In certain embodiments, the testicular cells are transplanted on Day 7 following ablation.

In a fifth aspect, the present invention provides a method of treating infertility in a subject, comprising ablating the endogenous Sertoli and germ cells of the subject and subsequently transplanting previously collected testicular cells of the subject into the testis of the subject, wherein spermatogenesis is induced in the subject. In certain embodiments, the testicular cells are transplanted on Day 7 following ablation.

In a sixth aspect, the present invention provides a method of reconstructing spermatogenesis of a subject comprising ablating the endogenous Sertoli and germ cells of a host and subsequently transplanting testicular cells of the subject into the testis of the host, wherein spermatogenesis of the SSCs of the subject is induced in the host. In certain embodiments, the testicular cells are transplanted on Day 7 following ablation.

In a seventh aspect, the present invention provides a method of treating infertility in a subject, comprising ablating the endogenous Sertoli and germ cells of a host and subsequently transplanting testicular cells of the subject into the testis of the host, wherein spermatogenesis of the SSCs of the subject is induced in the host. In certain embodiments, the testicular cells are transplanted on Day 7 following ablation.

In an eighth aspect, the invention provides a method for the selective depletion of epithelial cells in a tissue, comprising administering to the subject an effective amount of BC. The invention also provides a method for treating a disease or disorder associated with damaged epithelial cells in a subject comprising selectively depleting damaged epithelial cells in a tissue by administering to the subject an effective amount of BC.

BRIEF DESCRIPTION OF THE DRAWINGS

The accompanying drawings are included to provide a further understanding of the methods and compositions of the disclosure, and are incorporated in and constitute a part of this specification. The drawings illustrate one or more embodiment(s) of the disclosure, and together with the description serve to explain the principles and operation of the disclosure.

DETAILED DESCRIPTION OF THE INVENTION

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

It is also to be understood that unless clearly indicated otherwise by the context, embodiments disclosed for one aspect or embodiment of the invention can be used in other aspects or embodiments of the invention as well, and/or in combination with embodiments disclosed in the same or other aspects of the invention. Thus, the disclosure is intended to include, and the invention includes, such combinations, even where such combinations have not been explicitly delineated.

Definitions

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising/* or "having" certain elements are also contemplated as "consisting essentially of and "consisting of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. In some embodiments, the disorder comprises infertility.

The term "effective amount" or "therapeutically effective amount" refers to an amount sufficient to effect beneficial or desirable biological and/or clinical results. In some instances, for example, the beneficial or desirable biological and/or clinical result is the substantial depletion of the testis of Sertoli cells within 4 days of administration of BC, such that the testis allow for engraftment of donor cells and the generation of sperm.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. It will be clear from context that in most instances use of the terms "subject" and "patient" refer to male animals.

As used herein, the term "rescuing endogenous spermatogenesis" refers to inducing spermatogenesis from the SSCs within the testis of a subject who suffers from infertility, including infertility due to Sertoli cell dysfunction.

The term "reconstructing spermatogenesis of a donor" refers to inducing spermatogenesis of SSCs of a donor subject through engraftment of donor testicular cells, and is not intended to be limited to induction within a particular entity or host.

As used herein, the term "previously collected testicular cells" refers to viable testicular cells that were collected and stored, e.g. were cryopreserved, or to viable testicular cells that are derived from testicular tissue that was collected and was stored, e.g. was cryopreserved. In this context, testicular tissue is meant to include tissue from immature testes. For example, "previously collected testicular cells" can be used to refer to testicular cells derived from testicular tissue of a subject that was collected and stored prior to the subject undergoing chemotherapy. The previously collected testicular cells used in the methods of the invention may have been dissociated from testicular tissue prior to storage, i.e. isolated, cryopreserved, and then thawed for use, or they may be generated from testicular tissue fragments that were cryopreserved and then thawed, and then processed to collect the testicular cells for use in the methods disclosed herein.

Unless otherwise defined, all technical terms used herein have the same meaning as commonly understood by one of ordinary skill in the art to which this disclosure belongs.

Ablation of Sertoli Cells and Related Methods

The inventors have surprisingly discovered that benzalkonium chloride (BC), which is non-toxic, can be used to ablate Sertoli cells in the testes of a subject. In particular, in some instances Sertoli cells can be ablated in a selective fashion, wherein Sertoli cells are ablated in the subject while other cells such as SSCs are not affected. The inventors have also surprisingly discovered that engraftment of a subject with isolated donor Sertoli cells on Day 4 following treatment with BC results in rescue of spermatogenesis, providing a mechanism for the treatment of infertility in a subject suffering from Sertoli cell dysfunction.

The inventors have further discovered that on Day 7 following treatment with BC, not only are Sertoli cells ablated, but germ cells are ablated as well, and other cell types in the testis are variably affected. The inventors have also surprisingly discovered that engraftment of a host with donor testicular cells—either fresh or cryopreserved and thawed—on Day 7 following treatment of the host testis with BC, results in engraftment of Sertoli and other cell types and spermatogenesis of the donor SSCs, providing a mechanism for addressing infertility or conducting xenogeneic transplantation.

The inventors have also discovered that treatment with BC can effect selective depletion of epithelial cells in other tissues, providing a mechanism for the treatment of diseases associated with epithelial cells.

Accordingly, in a first aspect, the present invention provides a method for ablating Sertoli cells in a subject comprising administering to the subject an effective amount of BC. The BC may be present in solution and administered to the testis of the subject. In certain embodiments of the first aspect of the invention, selective Sertoli cell ablation (i.e. ablation of Sertoli cells with no or only a partial effect on other cells such as SSCs) is achieved at Day 4 following administration of the BC solution.

The American College of Toxicology has concluded that BC can be safely used as an antimicrobial agent at concentrations up to 0.1%. BC has been in clinical use since 1935 and is contained in a wide variety of prescription and over-the-counter products (Marple, B., et al. *Otolaryngology—head and neck surgery: official journal of American Academy of Otolaryngology—Head and Neck Surgery* 130: 131-141 (2004)). BC was previously reported to remove the mouse and rat enteric nerve plexus when the GI tract was treated in vivo (Sato, A., et al. *Journal of pediatric surgery* 13: 399-435 (1978); Sakata, K., et al. *Experientia* 35: 1611-1613 (1979); Fox, D. A. & Bass, P. *Gastroenterology* 87: 572-577 (1984); Yoneda, A., et al. *Pediatric Surgery International* 18: 234-237 (2002); Pan, W. K., et al. *The Journal of Surgical Research* 167: e221-230 (2011); Shu, X., et al. *Molecular Neurobiology* 48: 429-437 (2013)). Without wishing to be bound by any particular theory, the inventors believe that BC has a greater effect on cells that are more negatively charged, such as Sertoli cells, allowing for the membrane-charge-dependent selective ablation of Sertoli cells.

In certain embodiments of the first aspect and further aspects of the invention, the subject is a mammal, including human, bovine, equine, canine, feline, primate, rodent, porcine, and ovine animals. In certain embodiments, the subject is a mouse, a canine, or a human.

In this and further aspects of the invention, the BC solution may be administered locally to the testis by way of injection into the rete testis/seminiferous tubules of the testis.

The BC solution may comprise BC and any pharmaceutically acceptable carriers or excipients. Preferably, the BC solution is aqueous. For example, the BC may be administered in phosphate-buffered saline (PBS). The BC solution administered to the subject may have a concentration (% w/v) in the range of 0.001% to 0.1%. In some embodiments, the BC solution may have a concentration in the range of 0.004% to 0.06%, 0.01% to 0.03%, 0.02% to 0.03%, or the concentration may be about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, or about 0.1%, or any concentration range based on any two of these concentrations. The volume of BC solution to be administered can be readily determined by one of skill in the art. In a non-limiting example, 10-15 µl of BC solution may be administered into mouse testis.

In a second aspect, the present invention provides a method for rescuing endogenous spermatogenesis in a subject suffering from Sertoli cell dysfunction comprising ablating the endogenous Sertoli cells of the subject and subsequently transplanting donor Sertoli cells into the testis of the subject. In one embodiment of the second aspect of the invention, ablating the endogenous Sertoli cells is achieved by administering to the subject an effective amount of BC. In a further embodiment, the donor Sertoli cells are transplanted into the testis of the subject on Day 4 following administration of BC.

In a third aspect, the present invention provides a method for treating infertility in a subject comprising ablating the endogenous Sertoli cells of the subject and subsequently transplanting donor Sertoli cells into the testis of the subject, wherein endogenous spermatogenesis is induced in the subject. In one embodiment of the second aspect of the invention, ablating the endogenous Sertoli cells is achieved by administering to the subject an effective amount of BC. In a further embodiment, the donor Sertoli cells are transplanted into the testis of the subject on Day 4 following administration of BC. In one embodiment of this aspect of the invention, the infertility is idiopathic and in a further embodiment, the infertility is due to Sertoli cell dysfunction.

In certain embodiments of the second and third aspects of the invention, the transplanted donor Sertoli cells are autologous dysfunctional Sertoli cells that have been repaired. In other embodiments of the second and third aspects of the invention, the transplanted donor Sertoli cells are exogenous, and may be allogeneic or xenogenic.

An ultrasound-guided seminiferous tubule transplantation technique has already been established for primates and humans (Brook, P. F., et al. *Fertil Steril* 75: 269-274 (2001)), and may be used in conjunction with the present invention. In a non-limiting example, Sertoli cells used for engraftment could be derived via an induced pluripotent cell (iPSC) strategy (Buganim, Y., et al. *Cell Stem Cell* 11: 373-386 (2012)) to avoid immune rejection. In cases where the defect in Sertoli cells is identified through whole exon sequencing and cross-referencing with known Sertoli essential genes (eg. KITL), it could be corrected via CRISPR in iPSCs prior to re-transplantation following BC ablation. Alternatively, it may be possible to use allogeneic and xenogeneic grafts, wherein it would be unnecessary to derive and repair host Sertoli cells to rescue infertility due to Sertoli cell defects. Instead, any donor could be used.

In a fourth aspect, the present invention provides a method of reconstructing spermatogenesis of a subject comprising ablating the endogenous Sertoli and germ cells of the subject and subsequently transplanting previously collected testicular cells of the subject into the testis of the subject.

In a fifth aspect, the present invention provides a method of treating infertility in a subject, comprising ablating the endogenous Sertoli and germ cells of the subject and subsequently transplanting previously collected testicular cells of the subject into the testis of the subject, wherein spermatogenesis is induced in the subject.

In one embodiment of the fourth and fifth aspects of the invention, ablating the endogenous Sertoli cells and germ cells of the subject is achieved by administering to the subject an effective amount of BC. In a further embodiment, the testicular cells of the subject are transplanted into the testis of the subject on Day 7 following administration of BC.

In a sixth aspect, the present invention provides a method of reconstructing spermatogenesis of a subject comprising ablating the endogenous Sertoli and germ cells of a host and subsequently transplanting testicular cells of the subject into the testis of the host, wherein spermatogenesis of the SSCs of the subject is induced in the host.

In a seventh aspect, the present invention provides a method of treating infertility in a subject, comprising ablating the endogenous Sertoli and germ cells of a host and subsequently transplanting testicular cells of the subject into the testis of the host, wherein spermatogenesis of the SSCs of the subject is induced in the host.

In one embodiment of the sixth and seventh aspects of the invention, ablating the endogenous Sertoli cells and germ cells of a host is achieved by administering to the host an effective amount of BC. In a further embodiment, the testicular cells of the subject are transplanted into the testis of the host on Day 7 following administration of BC. In yet another embodiment of these aspects of the invention, the transplanted testicular cells are previously collected testicular cells. In certain embodiments of these aspects of the invention, the host is an immune deficient host, e.g. an immune deficient mouse.

In one embodiment of the fifth and seventh aspects of the invention, the infertility is a result of chemotherapy treatment for cancer, including pediatric cancer.

In the methods described in the fourth, fifth, sixth, and seventh aspects of the invention, the transplanted testicular cells of the subject will minimally contain SSCs and Sertoli cells, but may also include other testicular cells, such as other somatic cell types. The transplanted testicular cells may be fresh, or they may have been previously collected and cryopreserved and thawed, or derived from cryopreserved and thawed testicular tissue. In some instances, the SSCs of the subject will have been cryopreserved prior to transplantation, and in other instances the Sertoli cells will have been cryopreserved prior to transplantation.

In non-limiting examples, these methods may be used to treat infertility in an adult survivor of pediatric cancer who underwent chemotherapy, i.e. by cryopreserving a portion of the immature testis of the patient prior to chemotherapy, and transplanting the pre-chemotherapy testicular cells back into the testis of the patient later in life, or by transplanting the testicular cells into a host, e.g. a mouse, for production of sperm. In some instances, to reduce the risk of cancer recurrence, FACS could be used to deplete residual lymphocytes from the testicular cell containing sample prior to transfer back to patient's own testis.

The methods may also be used for xenogenic production of sperm, e.g. the production of sperm from humans or from endangered species in mice. Since seminiferous transplantation was developed by Brinster (Brinster, R. L. & Zimmermann, J. W. *Proc Natl Acad Sci USA* 91: 11298-11302 (1994)), xenogeneic transplantation has been investigated. Although human and piglet SSCs attached to the mouse testis basement membrane and remained for several months, they did not show further maturation (Dobrinski, I., et al. *Biol Reprod* 61: 1331-1339 (1999); Dobrinski, I., et al. *Mot Reprod Dev* 57: 270-279 (2000); Nagano, M., et al. *Fertil Steril* 78: 1225-1233 (2002)). Accordingly, mouse Sertoli cells and other supporting cells cannot support xenogeneic SSCs. However, the inventors have discovered that transplantation of both supporting cells and SSCs from a xenogeneic donor is permissive for development of donor spermatogenesis after ablation of endogenous Sertoli cells and SSCs by BC treatment. Donor Leydig cells and PMCs colonized in their normal interstitial environment in the host testis. These donor supporting cells may provide a more comfortable niche for xenogeneic donor SSCs in a host mouse testis. Thus, this approach may be used for fertility preservation for young cancer patients. Alternatively, it might be possible to use a "humanized" testis environment (e.g. "humanized" non-human testis such as mouse testis) to support the maturation of human primordial germ cell like cells (hPGCLCs) developed from pluripotent stem cells (PSCs) in vitro (Sasaki, K., et al. *Cell Stem Cell* 17: 178-194 (2015)).

In an eighth aspect, the invention provides a method for the selective depletion of epithelial cells in a tissue, comprising administering to the subject an effective amount of BC. This aspect of the invention also provides a method for treating a disease or disorder associated with damaged epithelial cells in a subject comprising selectively depleting damaged epithelial cells in a tissue by administering to the subject an effective amount of BC. As used herein, "damaged epithelial cells" are any abnormal epithelial cells, including cancerous cells. This method may further comprise repopulating the epithelial cells in the tissue with undamaged cells by transplanting donor epithelial cells in the tissue following depletion of the damaged epithelial cells in the tissue of the subject.

In one embodiment of the eighth aspect of the invention, the tissue is kidney, GI tract, liver or lung tissue, or the bladder. In another embodiment of this aspect of the invention, the BC solution is administered locally to the tissue, for example by direct injection into the tissue. The volume and concentration of the BC solution administered to the tissue can determined by one of skill in the art. In a non-limiting example, 20-40 μl of BC solution may be administered into a mouse bladder.

Diseases or disorders associated with damaged epithelial cells are known in the art and include, but are not limited to, chronic renal disease, cancers of the GI tract (e.g. esophageal cancer, gastric cancer, and colon cancer), and other epithelial diseases in organs such as kidney, GI tract, liver, lung, or the bladder.

EXAMPLES

Example 1: Methods

Animals

ICR outbred, and C57BL/6J and FVB inbred strains, and CAG-EGFP, SF1-EGFP, Sox9-ECFP, Oct4-GFP and Dnd1-EGFP transgenic mice were used. Because Sox9-ECFP transgenic mice are maintained on a C57BL/6J background, for Sertoli cell transplantation experiments, adult C57BL/6J or F1(FVB×C57BL/6J) were used as hosts. The Sox9-ECFP mouse pups were used as donors at 6.5-10.5 day postpartum. Because CAG-EGFP transgenic mice are maintained on an FVB background, for testicular cell transplantation experiments, adult FVB and F1(C57BL/6J×FVB) were used as hosts. Mice were housed in accordance with National Institutes of Health guidelines, and experimental protocols were approved by the Institutional Animal Care and Use Committee of Duke University Medical Center. Castrated 6 and 8 weeks old dog testis was provided from the animal protection society of Durham, N.C.

Drug Preparation

A commercially available solution (20% w/v) of benzalkonium chloride was obtained (CAS; 8001-54-5; Acros Organics) and diluted with PBS to prepare 0.02% and 0.03% solutions.

Testis Tissue Culture Method

Fragments of the mouse testis were incubated with 0.02% BC for 10 min. After washing several times with PBS, tissues were placed atop 1.5% agarose blocks (214530; Difco), prepared and placed in 6 well tissue culture plates (353046; Falcon) with ~500 μl of 10% FBS+DMEM (11995-065; Gibco) to reach halfway up the side of the block. After culture, tissues were washed in PBS and fixed for immunofluorescence. The dog testis tissues were incubated with 0.02% or 0.03% BC for 10 min and cultured with 10% KnockOut Serum Replacement (KSR) (Invitrogen; 10828-028)+DMEM (Yokonishi, T., et al. *Methods in Molecular Biology* 927: 479-488 (2013)). The culture incubator was supplied with 5% (vol/vol) carbon dioxide in air and maintained at 37° C.

Chemicals Used as Cell Death Inhibitors

Q-VD (OMe)-OPh (A8165; ApexBio), Necrostatin-1, Spautin-1 (Sigma; SML0440), 3-Methyladenine (Cayman; CAS 5142-23-4), LY294002 (Cayman; CAS 154447-36-6), Bafilomycin A1 (Cayman; CAS88899-55-2) were used as cell death inhibitors.

Testicular Cell Culture Method

Neonatal testes were enzymatically digested using 0.25% trypsin and 1 mM EDTA for 10 min at 37° C. The reaction was stopped by addition of serum and cells were washed twice. The cell suspension was filtered through 40 μm nylon mesh (352340; Falcon) and resuspended in 10% FBS+DMEM. Single cell suspensions were introduced onto 0.1% gelatin coated glass in a 24 well plate (353226; Falcon) for patch-clamp analysis.

Whole-Cell Electrophysiological Recordings

Resting potential (baseline states) in cultured testicular cells were recorded in current-clamp mode of a standard patch-clamp technique at room temperature (23-25° C.) using pClamp 10 software (Axon). Patch pipettes were pulled from borosilicate glass tubes to give a tip resistance of 3.5-7 MΩ filled with pipette solution containing 130 mM potassium gluconate, 2 mM NaCl, 4 mM MgCl2, 20 mM HEPES, 4 mM Na2ATP, 0.4 mM NaGTP, 0.5 mM EGTA. Once a gigaseal was formed, suction pulses were used to break the membrane patch to obtain the whole-cell configuration. The extracellular buffer contained 125 mM NaCl, 2.5 mM KCl, 2 mM $CaCl_2$, 1 mM $MgCl_2$, 25 mM $NaHCO_3$, 1.25 mM $NaH_2PO_4$, and 10 mM glucose, pH 7.3, and was continuously bubbled with 5% $CO_2$ and 95% $O_2$ during the experiment.

Drug Injection into Seminiferous Tubules

Host mice were anesthetized. A glass needle was back-loaded with the drug and 0.02% bromophenol blue to track the success of the injection and extent of delivery into the tissue. The mixture was injected into the rete-testis.

Donor Sertoli Cell Preparation

On the day of transplantation, FACS analysis was used to isolate donor Sertoli cells. Testes of Sox9-CFP mouse pups were dissected. Testicular cells were enzymatically dissociated using 1 mg/ml collagenase type IV for 15 minutes followed by incubation in 0.25% trypsin and 1 mM EDTA for 10 min at 37° C. The reaction was stopped by addition of serum and cells were washed twice. The cell suspension was filtered through a 40 µm nylon mesh and resuspended in 10% FBS+DMEM.

Cryopreservation and Thawing Method

After dissociation and washing steps, samples were placed in 2.0 ml cryovials (Corning, N.Y., USA) containing 500 µl of cryopreservation medium, (10% FBS+DMEM containing 10% DMSO). Samples were placed in a controlled freezing device (Mr. Frosty™ Freezing Container, Thermo Fisher Scientific) and cooled in a −80° C. freezer overnight. The following morning the cryovials were transferred to Liquid nitrogen for storage. Prior to use, samples were thawed quickly in a bath warmed to 37° C.

Testicular Cell Transplantation 10-15 µl of approximately $1 \times 10^6$/ml isolated Sertoli cells or $1 \times 10^8$/ml (testicular cells) were injected through the rete testis into the seminiferous tubules of a host mouse on day 4 or day 7 after ablation treatment. A glass needle was back-loaded with the cell suspension and 0.04% Trypan blue to track the efficiency of the injection.

Immunofluorescent Cytochemistry

For cultured neonatal mouse testes, whole-mount immunofluorescence analysis was performed. Samples were fixed overnight with 4% (wt/vol) paraformaldehyde in PBS at 4° C. After several washes in PBTx (PBS plus 1% Triton X-100), samples were incubated in blocking solution (1% PBTx plus 10% FBS and 3% BSA) for 1 h at room temperature. Primary antibodies were diluted in blocking solution and applied to samples for 2 days at 4° C. After several washes in 1% PBT, fluorescent secondary antibodies were applied for 2 days at 4° C.

Adult mouse testis and canine testis tissues were fixed in 4% (wt/vol) paraformaldehyde in PBS at 4° C. overnight and cryoembedded in OCT compound (Sakura Finetek). Samples were cut into 14-µm-thick cryosections. Incubation with primary antibodies was performed overnight at 4° C., followed by 2 washes, and incubation with secondary antibodies for 1 h at room temperature. Nuclei were counterstained with Hoechst 33342 dye. Samples were mounted on glass slides and imaged with a confocal laser microscope (Zeiss 780).

The following primary antibodies were used. Chicken antibodies against GFP (Ayes (GFP-1020); 1:1000), rabbit anti-SOX9 antibody (Millipore (AB5535); 1:2000), goat anti-SOX9 antibody (R&D (AF3075); 1:1000), mouse anti-F4/80 antibody (AbD Sertotec (MCA497RT); 1:1000), rat anti-TRA98 antibody (Abcam (ab82527); 1:1000), rabbit anti-Laminin antibody (kind gift of Harold Erickson; 1:500), rat anti-PECAM1 antibody (BD Bioscoeices (557395); 1:250), goat anti-KIT antibody (Novus Biologicals (AF1356); 1:100), goat anti-GFRa1 antibody (R&D (AF560); 1:100), rat anti-E-Cad antibody (Novus Biologicals (13-1900); 1:500), rabbit anti-MVH antibody (Abcam (ab13840); 1:500), human anti Hu C/D antibody (kindly Gifted from V. Lennon, Mayo Clinic, Rochester, USA; 1:10000), rabbit anti-γH2AX (Upstate (05-636); 1:500), PNA (Novus Biologicals (LS-C69213); 1:600), rabbit monoclonal anti-caspase-3 (Cell Signaling (9661S); 1:500). Rabbit anti-3βHSD antibody (TrasnGenic Inc (KO607); 1:100;), rabbit anti Stra8 antibody (kindly provided by Pierre Chambon, Institute for Genetics and Cellular and Molecular Biology, Strasbourg, France; 1:1000), mouse anti GATA-4 antibody (Santa Cruz Biotechnology (SC25320); 1:500), mouse Cy3 conjugated anti-α-Smooth Muscle Actin (Sigma (C-6198); 1:500) antibody and rabbit anti KI67 antibody (Thermo Scientific (RM-9106-S); 1:500). The secondary antibodies used were goat anti-mouse IgG2a (Invitrogen (A21241); 1:500), goat anti-rat IgG (Invitrogen (A21434); 1:500), goat anti-rabbit IgG (Invitrogen (A21244); 1:500), goat anti-rabbit IgG (Invitrogen (A21429); 1:500), goat anti-rabbit IgG (Invitrogen(A-11008) 1:500), donkey anti-chicken IgY (Jacksom ImmunoResearch (703-545-155); 1:500), donkey anti-goat IgG (Invitrogen (A21447) 1:500), anti-human conjugated to Alexa 488, Alexa 555 or Alexa 647.

Example 2: Ablation of Sertoli Cells by Benzalkonium Chloride

Neonatal Sertoli Cell Selective Depletion In Vitro.

Figure 1:
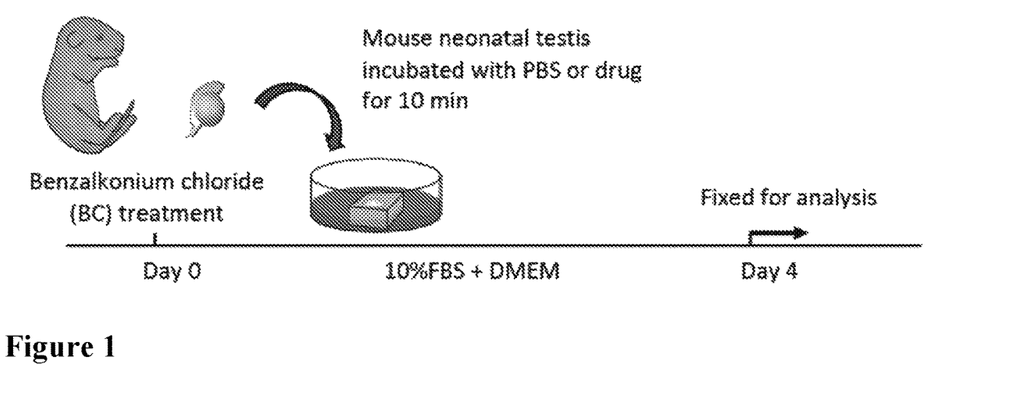
FIG. 1. Schematic representation of experimental procedures for in vitro Sertoli cell ablation.

We incubated a neonatal testis in 0.02% BC solution for 10 min (or PBS as a control), washed the testis several times with PBS and cultured for 4 days at the surface/air interface in wells atop an agarose block (FIG. 1). At the end of that time, the testis was fixed and stained for immunofluorescence analysis using an antibody against the Sertoli cell marker, SOX9 (Sry-box 9). This analysis showed that BC specifically eliminated Sertoli cells. Although the number of F4/80 positive macrophages was increased in the interstitium of drug treated testis, other cell types in the testis including GFRα1 (GDNF family receptor al) and E-CAD (Cadherin1)-positive SSCs, and 3βHSD (3β-hydroxysteroid dehydrogenase)-positive Leydig cells were spared.

Sertoli Cells Carry a Negative Charge Relative to Other Testicular Cells.

Figure 2:
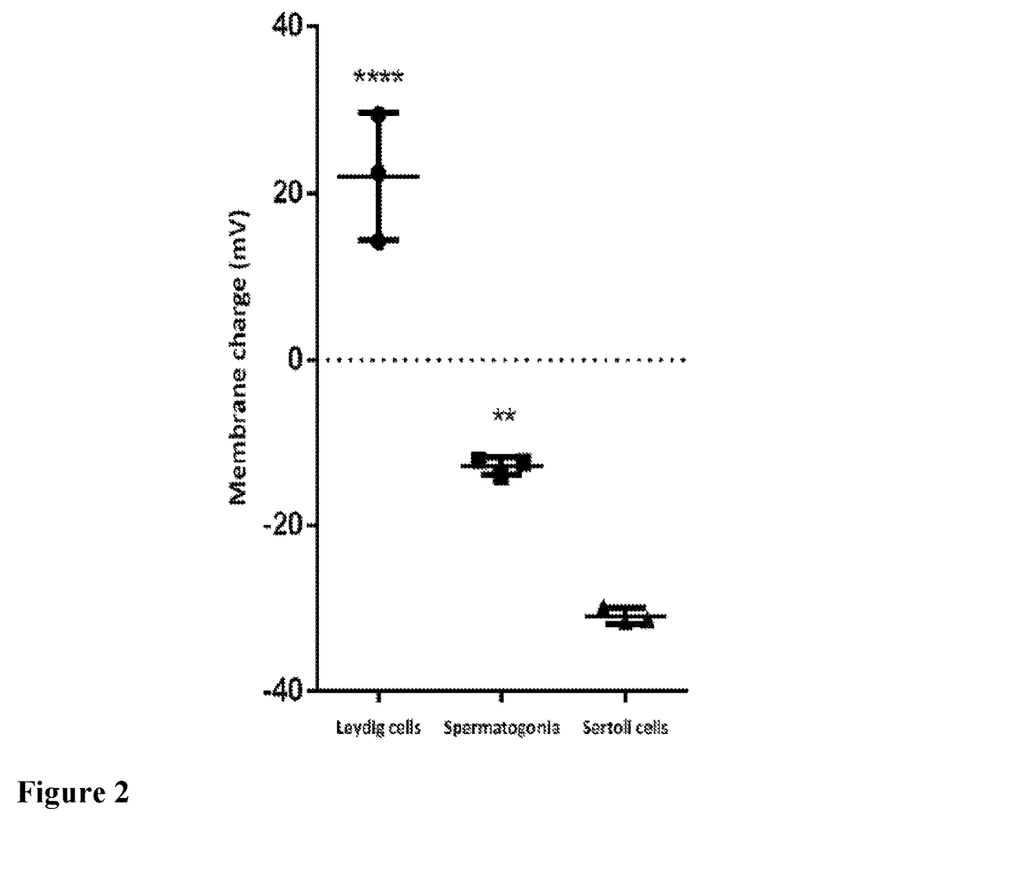
FIG. 2. The average membrane potential of each cell type (Leydig cells, Spermatogonia, and Sertoli cells). Data represent the mean±SD of biological triplicate experiments. $P \leq 0.01$, $**P \leq 0.0001$. Statistical analysis was performed using one-way ANOVA, followed by Dunnett's multiple comparison test.

Because BC is a cationic surfactant that works preferentially on cells with strong negative membrane charge (Sato, A., et al. *Journal of Pediatric Surgery* 13: 399-435 (1978)), we tested whether the Sertoli cell membrane has a more negative charge than other cell types in the testis. We conducted targeted patch-clamp analysis to measure the membrane potential of cultured testicular cells isolated from transgenic lines carrying SF1-EGFP (in which gating for bright cells isolates Leydig cells), Oct4 (Pou5f1; POU domain, class 5, transcription factor 1)-GFP (a marker for SSCs), and Sox9-ECFP (a marker for Sertoli cells). Patch clamp experiments comparing these cell types indicated that the Sertoli cell membrane potential was the most negative, approximately −30 mV, while spermatogonia had a negative charge of approximately −10 mV, and Leydig cells carried a positive charge of approximately 20 mV (FIG. 2).

BC Induces Autophagy in Sertoli Cells.

Figure 3:
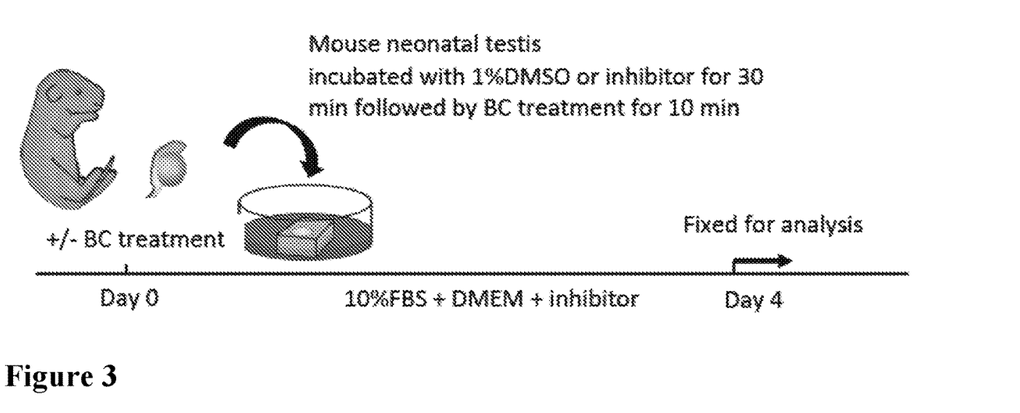
FIG. 3. Schematic representation of experimental procedures for inhibition of in vitro Sertoli cell ablation with BC.

Next, we investigated the Sertoli cell death pathway caused by BC treatment. Testes from neonatal pups were pre-treated with 1% DMSO (as a control) or with cell death pathway inhibitors, pan-caspase inhibitor, 2,6-difluorophenoxymethylketone-based inhibitor (Q-VD-OPH), necrosis inhibitor (Necrostatin-1) and autophagy inhibitors, Spautin-1, LY294002, or Bafilomycin A1, for 30 min. Pre-treatments were followed by a 10 min BC treatment, washing, and culture in the presence of the inhibitor for 4 days (FIG. 3). Whereas inhibitors of cell death pathways or necrosis (or the control) did not impede the effect of BC, i.e. they did not rescue Sertoli cells after BC treatment, inhibitors of the early phases of autophagy, Spautin-1, LY294002 and 3MA, and the late phase of autophagy, Bafilomycin A1, partially rescued Sertoli cells.

Example 3: Depletion of Canine Sertoli Cells In Vitro

Figure 4:
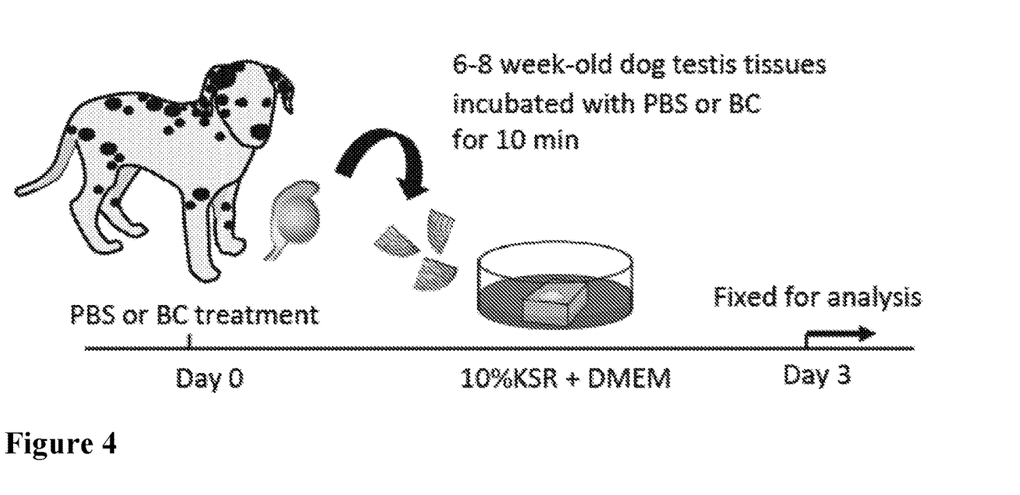
FIG. 4. Schematic representation of experimental procedures for in vitro canine Sertoli cell ablation.

We used the same procedure as described for the mouse testis to test whether BC could eliminate Sertoli cells from canine testis. Six to 8 week-month-old canine testis tissues were cut into fragments and incubated with 0.02% or 0.03% BC for 10 min (or PBS as a control), washed, and cultured for 3 days (FIG. 4). At the end of that time, the testis was fixed and stained for immunofluorescence analysis using antibodies against SOX9 and the germ cell marker, MVH (mouse vasa homolog). In control tissue, both Sertoli cells and germ cells were detected in seminiferous tubules. However, in 0.02% BC-treated testis tissue, Sertoli cells were depleted, particularly from the peripheral regions of the tissue. In 0.03% BC treated tissues, all Sertoli cells were absent, but some SSCs survived in Sertoli-depleted seminiferous tubules, where tubule structure was well maintained. In control canine testis, GATA-4 positive PMCs and Leydig cells were detected between tubules. However, 0.03% BC treatment caused some PMC depletion, and reduced the number of SSCs and Leydig cells.

Example 4: Sertoli Cells were Eliminated, but Testis Cord Structure, Vasculature, and Other Germ Cell Niche Components Remained Intact 4 Days Post BC Treatment Adult Sertoli Cell Depletion In Vivo.

Figure 5:
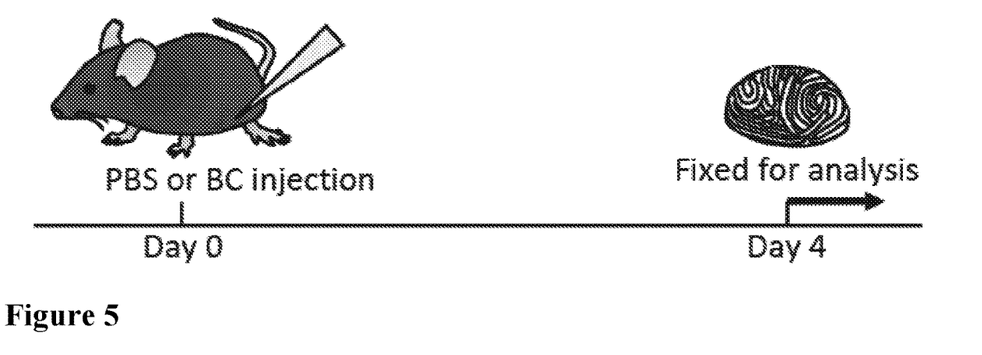
FIG. 5. Schematic representation of experimental procedures for in vivo adult Sertoli cell ablation.

We injected a solution of 0.02% BC (or PBS as a control) into the rete testis of anesthetized adult male mice to test the effects of the drug on adult Sertoli cells. To detect Sertoli cells easily, we used a Sox9-ECFP transgenic mouse (FIG. 5). On day 3 after BC treatment, abnormal cells with condensed DNA were observed in the lumen of the seminiferous tubules, but Sertoli cell depletion was not detected 3 days after drug treatment based on SOX9 expression. However, four days after treatment, Sertoli cells had disappeared from approximately 30-40% of seminiferous tubules.

Although some germ cells were positive for Caspase-3 on day 4, we did not detect Caspase3 positive Sertoli cells 4 days after treatment, consistent with the idea that BC does not induce apoptosis in Sertoli cells. Even though a well-organized germ cell layer was lost on day 3, macrophage invasion and proliferation were not observed until day 4, when many macrophages positive for F4/80 surrounded the affected tubules and some had invaded inside, where they may have scavenged dying Sertoli cells and spermatocytes. Antibodies against SMA (Smooth Muscle Actin, Alpha) suggested that PMCs were intact, and staining with anti-Laminin (LMN) antibody indicated that the basic tubular structure was also intact. Antibodies against 3βHSD and PECAM1 (Platelet/Endothelial Cell Adhesion Molecule 1) revealed that Leydig cells and endothelial cells were not obviously affected. Although loss of Sertoli cells resulted in the rapid loss of differentiating germ cells, some SSCs were found along the basal lamina in drug affected tubules based on straining with antibodies against STRA8 (Stimulated by Retinoic Acid gene 8), and Hu C/D (Human HuC/HuD neuronal protein) and c-KIT. We have seen no apparent system-wide effects after drug injection into the mouse rete testis.

In this study, BC injection caused no discernable side effects in the mouse. Our drug-induced ablation method appears to be a safe approach that induces severe Sertoli cell depletion in mice and canines.

In summary, 4 days after 0.02% BC treatment, Sertoli cells were eliminated, but the interstitional compartment, testis cord structure, and some spermatogonia were still present.

Figure 6:
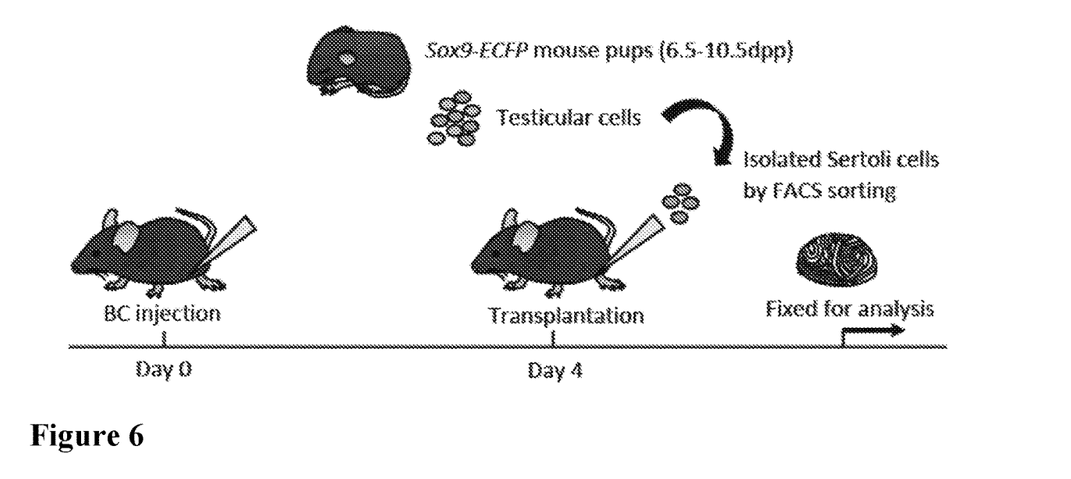
FIG. 6. Schematic representation of experimental procedures for transplant of Sertoli cells into adult testis 4 days after BC treatment.

Example 5: Host Spermatogenesis was Rescued by Sertoli Cells Introduced 4 Days Post BC Treatment To determine whether donor Sertoli cells can efficiently engraft drug-depleted cords, we transplanted Sertoli cells from 6.5-10.5 dpp Sox9-ECFP mouse pups. The host mouse was prepared by injection of the 0.02% BC solution 4 days prior to transplantation. Cells from a neonatal Sox9-ECFP donor testis were dissociated by enzymatic treatment, Sertoli cells were isolated by FACS, and injected into host seminiferous tubules through the rete testis (FIG. 6). After transplantation on day 0, some clusters of donor cells were found in the lumen of seminiferous cords. However, some donor cells resided on the basal lamina of testis tubules. Twelve days after transplantation, donor Sertoli cells replaced endogenous Sertoli cells and surrounded host SSCs. Thirty-three days after transplantation, donor Sertoli cells were present near host spermatogonia that had differentiated to primitive spermatids based on PNA (peanut agglutinin) staining morphology. Full spermatogenesis was detected 8 weeks after transplantation in 2 of 4 engrafted testes.

Example 6: Sertoli Cells and SSCs were Eliminated, but Patent Tubules Remained 7 Days Post BC Treatment We used a DND1 (dead end homolog 1)-EGFP mouse to investigate SSC kinetics after BC treatment. In this transgenic mouse, all SSCs including undifferentiated SSCs and differentiating spermatogonia express EGFP. 0.02% BC (or PBS control) was injected into seminiferous tubules of adult testis. Three days after Sertoli cells were depleted, SSCs had also disappeared. Although Sertoli cells and germ cells were lost in drug affected tubules, cord structure, Leydig cells, and PMCs were normal.

Figure 7:
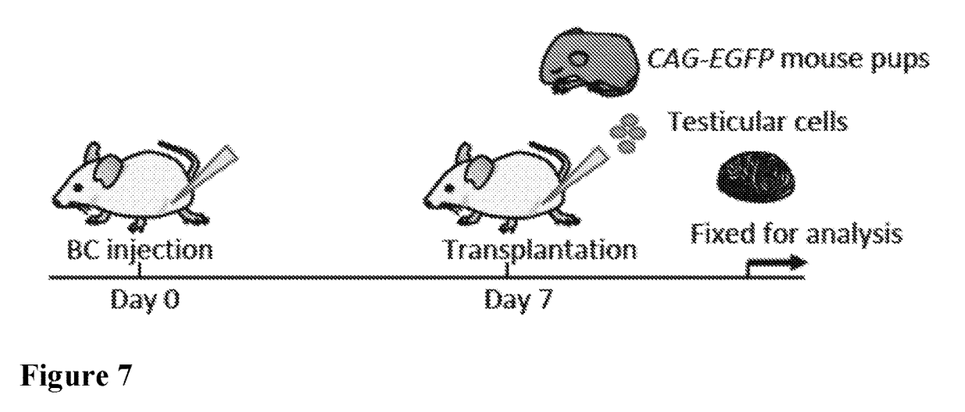
FIG. 7. Schematic representation of experimental procedures for testicular cell transplantation 7 days after BC treatment.

Example 7: Donor Spermatogenesis was Achieved Following Transplantation of Testicular Cells in Host 7 Days Post BC Treatment To determine whether the host testes depleted for both Sertoli and germ cells could be used as a scaffold for engraftment of multiple cell types, we performed testicular cell transplantation 7 days post BC treatment (FIG. 7). Nineteen days after testicular cell transplantation from CAG-EGFP pups into a treated host testis, donor Sertoli cells and SSCs colonized. Donor SSCs proliferated with support from donor Sertoli cells, initiated meiosis, and progressed to the spermatocyte stage. EGFP positive leptotene and pachytene spermatocyte were detected. Other donor testicular cells, negative for SOX9, were observed around the tubules where donor Sertoli cells and SSCs colonized. Most of these interstitial EGFP bright donor cells were Leydig cells, and some donor PMC colonization was also detected. Eight weeks after transplantation, PNA positive spermatids were observed in tubules where donor Sertoli cells and SSCs colonized. Round spermatids and elongated spermatids generated from donor SSCs with support from donor Sertoli cells were detected in the host testis. In 9/13 testes, donor Sertoli cell and SSC colonization was observed, and full spermatogenesis was detected in 4 of these hosts.

Cryopreserved Donor Testicular Cell Transplantation into BC Treated Testis.

It is known that cryopreserved SSCs colonize and undergo spermatogenesis (Avarbock, M. R., et al. *Nat Med* 2: 693-696 (1996)). We showed that cryopreserved Sertoli cells, Leydig cells, and PMCs were also able to colonize, regenerate the germ cell niche and support spermatogenesis. Replacement of many cell types comprising the germ cell niche makes it possible, e.g., to produce human sperm in a mouse testis from cryopreserved tissue of pre-pubertal donors.

Figure 8:
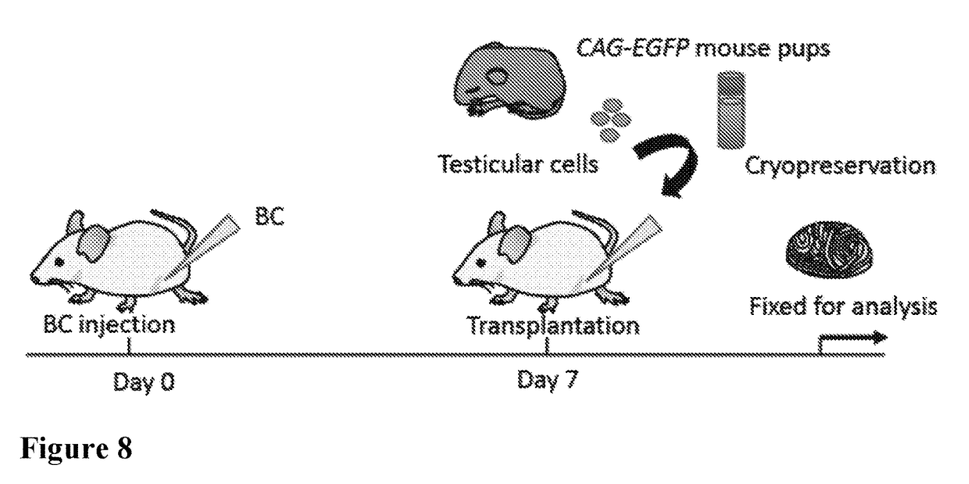
FIG. 8. Schematic representation of experimental procedures for cryopreserved testicular cell transplantation into BC treated testes.

To test the efficiency of engraftment using cryopreserved donor tissue, we dissociated testis tissue from CAG-EGFP pups, and cryopreserved cells with cryoprotectant including 10% DMSO in liquid nitrogen. Seven days after BC treatment of wild type host mice, cryopreserved (39 days) donor testicular cells were thawed and introduced into the rete testis (FIG. 8). Eight weeks after transplantation, we found that cryopreserved Sertoli cells and SSCs had colonized testis tubules and donor supporting cells presumably Leydig cells and PMCs were found in the interstitium. In some tubules, cryopreserved Sertoli cells supported host spermatogenesis, and in other tubules, cryopreserved donor Sertoli cells colonized with donor SSCs and supported donor spermatogenesis. In 3/3 host testes, cryopreserved Sertoli cells and SSCs colonized, and full spermatogenesis from donor cells was observed in 2 of these hosts.

Example 8: Epithelial Cell Ablation in Other Tissues by BC

Figure 9:
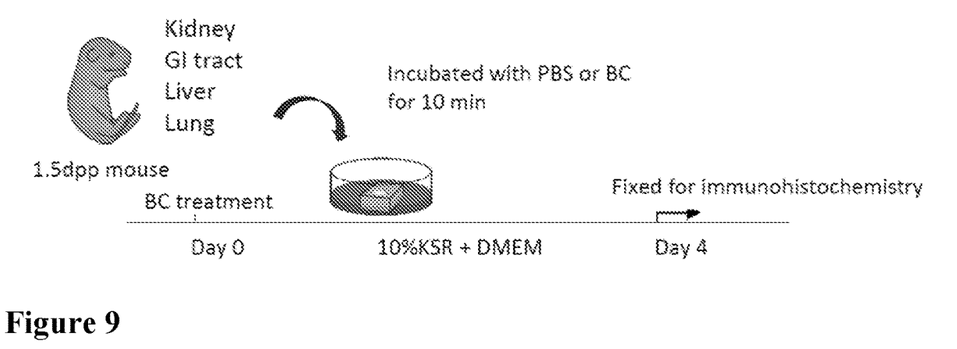
FIG. 9. Schematic representation of experimental procedures for in vitro epithelial cell ablation.

Methods
Animals:
ICR outbred, and C57BL/6J and FVB inbred strains.
Drug Preparation:
A commercially available solution (20% w/v) of benzalkonium chloride was obtained (CAS; 8001-54-5; Acros Organics) and diluted with PBS to prepare 0.004%-0.03% solutions.
Tissue Culture Method:
Fragments of the mouse kidney, GI tract, liver and lung were incubated with 0.03% BC for 10 min. After washing several times with PBS, tissues were placed atop 1.5% agarose blocks (214530; Difco), prepared and placed in 6 well tissue culture plates (353046; Falcon) with ~500 μl of 10% KnockOut Serum Replacement (KSR) (Invitrogen; 10828-028)+DMEM (11995-065; Gibco) to reach halfway up the side of the block. After culture, tissues were washed in PBS and fixed for immunofluorescence. The culture incubator was supplied with 5% (vol/vol) carbon dioxide in air and maintained at 37° C.
BC Injection into Bladder:
2 months old female mice were anesthetized using Avertin or Isoflurane as anesthetic. Using forceps, the top of the urethral orifice was pinched and pulled up without obstructing the urethra at a ~45° angle. The catheter tubing end was attachded to a 1 mL syringe, and the tip of the tubing rubbed in medicine mineral jelly. The jelly-topped catheter was carefully inserted into the urethra at a ~45° angle. The syringe was detached from the catheter, and the mouse's stomach was palpated to produce urine. Using another syringe and catheter, the urine that is produced was aspirated, and emptied into other towel. 20 uL of the BC solution (or PBS) was pipetted directly into the catheter using a pipet tip. It was ensured that the pipet tip contacted the catheter, then the cylinder was fully depressed for ~3 seconds. The liquid was pushed into the bladder by injecting ~20 uL of air using a syringe. The catheter was removed and the mouse put back into its cage.
BC Effect on Epithelial Cells in Other Organs.
We incubated a neonatal kidney, GI tract, liver and lung tissues in 0.03% BC solution for 10 min, washed the tissues several times with PBS and cultured for 4 days at the surface/air interface in wells atop an agarose block (FIG. 9). At the end of that time, the tissues were fixed and stained for immunofluorescence analysis using an antibody against E-CAD (Cadherin1), epithelial marker. This analysis showed that BC specifically eliminated epithelial cells. Although epithelial cells were eliminated in drug treated tissues, LMN (laminin) positive basement membrane and stromal cells which is stained with PDGFRβ were maintained.

We injected a solution of 0.004%, 0.06% BC into the bladder of anesthetized adult female mice to test the effects of the drug on bladder epithelial cells, urothelium. On day 6 after 0.06% BC treatment, urothelium detachment was observed in the lumen of the bladder, but urothelium depletion was not detected in control or 0.004% BC injected bladder. However, six days after treatment, urothelium had disappeared from approximately 80% of 0.06% BC treated bladder, some mesenchymal cells were found on straining with antibodies against PDGFRβ and NG2. Macrophage invasion were observed in 0.03% BC treated bladder, however, 0.004% BC treatment did not cause inflammation.

Figure 10:
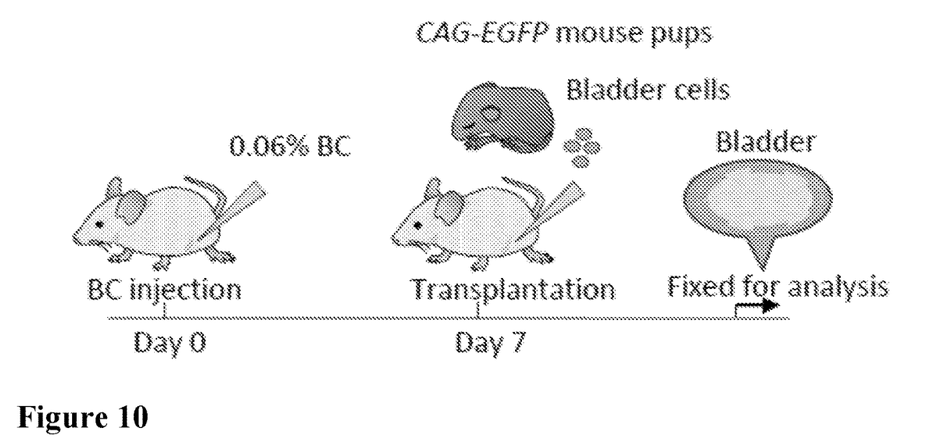
FIG. 10. Schematic representation of experimental procedures for repopulating epithelial cells in BC treated bladder.

Repopulation of Epithelial Cells in BC Treated Bladder.
CAG-EGFP mouse pup bladder cells are transplanted into BC treated bladder (FIG. 10).

We claim:
1. A method for ablating Sertoli cells in a subject, the method comprising administering to the subject an effective amount of a solution of benzalkonium chloride (BC), wherein the BC solution is administered locally to the testis by injection into the seminiferous tubules of the testis.

2. The method of claim 1 wherein the subject is a human.

3. A method for rescuing endogenous spermatogenesis in a subject suffering from Sertoli cell dysfunction, the method comprising:
(i) ablating the endogenous Sertoli cells of the subject, wherein ablation of the endogenous Sertoli cells is achieved by administering to the subject an effective amount of benzalkonium chloride (BC); and
(ii) subsequently transplanting donor Sertoli cells into the testis of the subject.

4. The method of claim 3 wherein the transplanted donor Sertoli cells are autologous dysfunctional Sertoli cells that have been repaired or are exogenous cells.

5. The method of claim 3 wherein the exogenous transplanted donor Sertoli cells are allogeneic or are xenogenic.

6. A method for treating infertility in a subject, the method comprising rescuing endogenous spermatogenesis in the subject according to the method of claim 3, wherein endogenous spermatogenesis is induced in the subject.

7. A method of reconstructing spermatogenesis of a subject, the method comprising:
(i) ablating the endogenous Sertoli and germ cells of the subject, wherein ablation of the endogenous Sertoli and germ cells is achieved by administering to the subject an effective amount of benzalkonium chloride (BC); and
(ii) subsequently transplanting previously collected testicular cells of the subject into the testis of the subject.

8. A method of treating infertility in a subject, the method comprising reconstructing spermatogenesis in the subject according to the method of claim 7, wherein spermatogenesis is induced in the subject.

9. A method of reconstructing spermatogenesis of a subject, the method comprising:
(i) ablating the endogenous Sertoli and germ cells of a host, wherein ablation of the endogenous Sertoli and germ cells is achieved by administering to the subject an effective amount of benzalkonium chloride (BC); and (ii) subsequently transplanting testicular cells of the subject into the testis of the host, wherein spermatogenesis of the spermatogenesis stem cells (SSCs) of the subject is induced in the host.

10. A method of treating infertility in a subject, the method comprising reconstructing spermatogenesis in the subject according to the method of claim 9, wherein spermatogenesis of the SSCs of the subject is induced in the host.

11. The method of claim 9 wherein the transplanted testicular cells are previously collected testicular cells.

12. The method of claim 9 wherein the infertility is a result of chemotherapy treatment for cancer.

* * * * *